United States Patent [19]
Bauer

[11] Patent Number: 5,688,229
[45] Date of Patent: Nov. 18, 1997

[54] CERVICAL COLLAR

[76] Inventor: Eric Bauer, P.O. Box 9150, Reno, Nev. 89507

[21] Appl. No.: 651,037

[22] Filed: May 17, 1996

[51] Int. Cl.⁶ ..................................................... A61F 5/00
[52] U.S. Cl. ............................ 602/18; 602/5; 128/DIG. 23
[58] Field of Search ..................... 128/DIG. 23; 602/5-6, 602/17-19, 23, 27; 24/580, 583

[56] References Cited

U.S. PATENT DOCUMENTS

| | | | |
|---|---|---|---|
| 3,024,784 | 3/1962 | Monfardini | 602/18 |
| 4,502,471 | 3/1985 | Owens | 602/18 |
| 4,543,947 | 10/1985 | Blackstone | 602/18 |
| 4,577,375 | 3/1986 | Beaussant | 24/583 X |
| 4,628,913 | 12/1986 | Lerman | 602/18 |
| 4,903,381 | 2/1990 | Fohl | 24/580 X |
| 4,969,453 | 11/1990 | Heimann | 602/18 |
| 5,097,824 | 3/1992 | Garth | 602/17 X |
| 5,201,702 | 4/1993 | Mars | 602/17 |
| 5,366,438 | 11/1994 | Martin, Sr. | 602/5 |
| 5,520,619 | 5/1996 | Martin | 602/5 |
| 5,531,669 | 7/1996 | Varnau | 602/18 |

Primary Examiner—Richard J. Apley
Assistant Examiner—Denise Pothier
Attorney, Agent, or Firm—David H. T. Wayment

[57] ABSTRACT

A cervical collar is disclosed. The collar has a chin support which can be adjusted up or down to accommodate necks of different lengths.

3 Claims, 6 Drawing Sheets

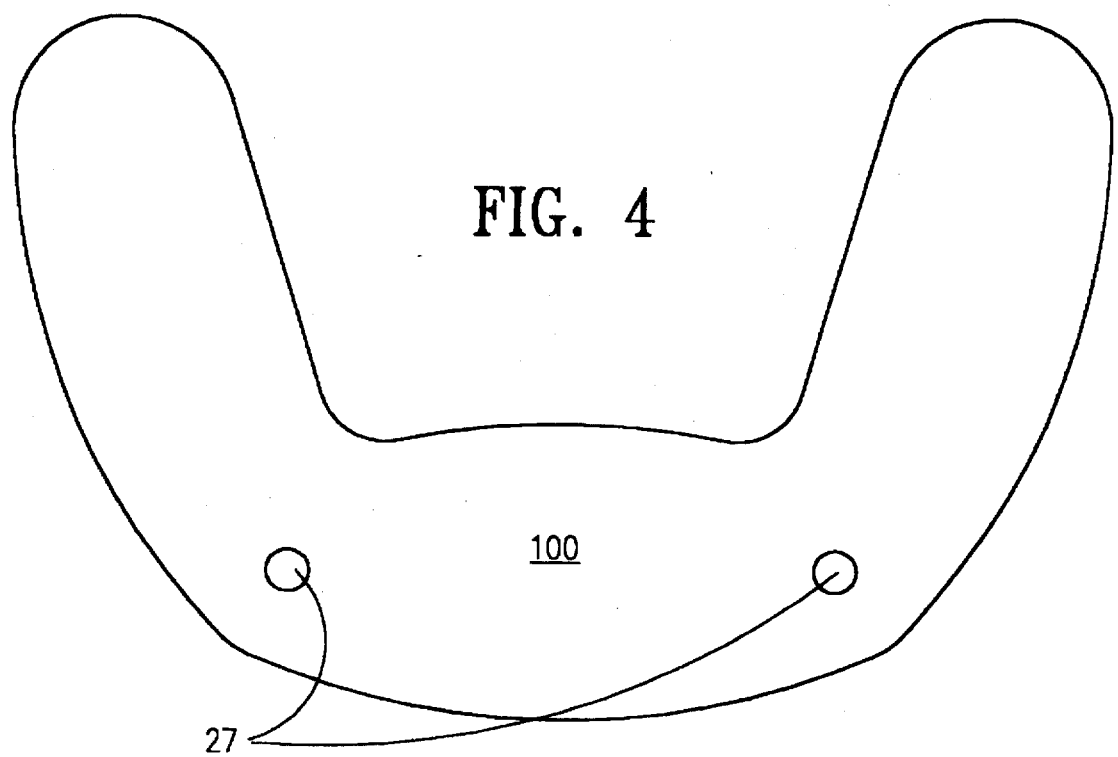
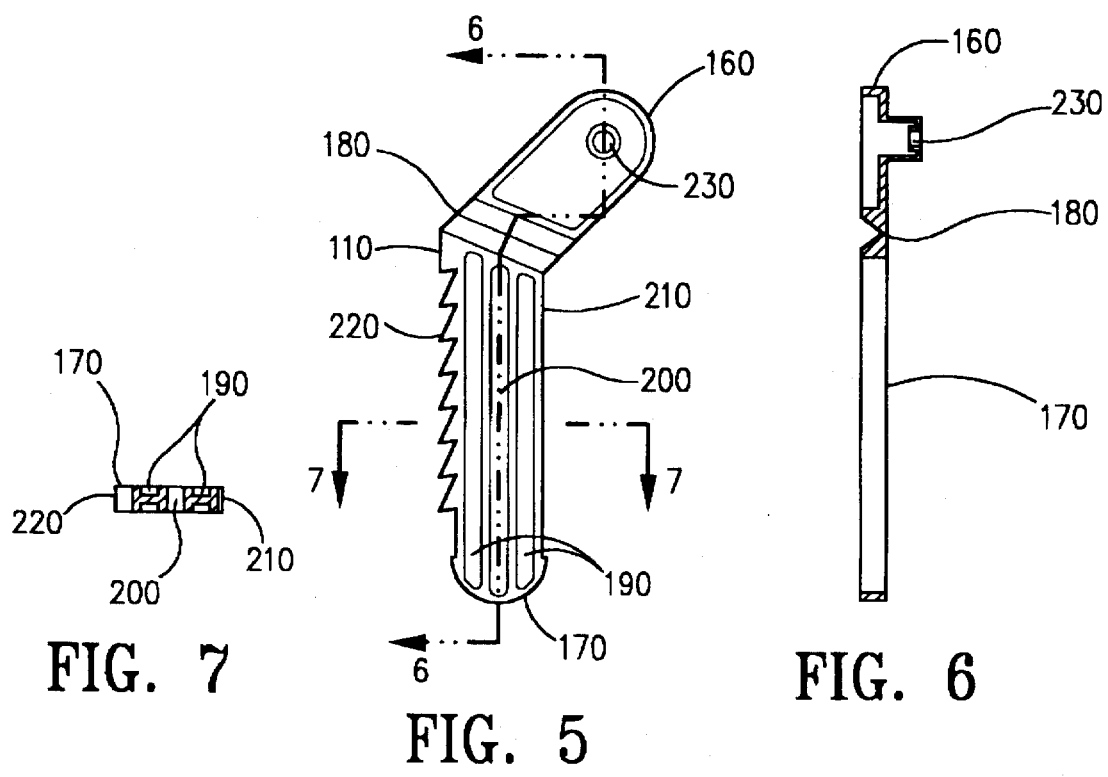

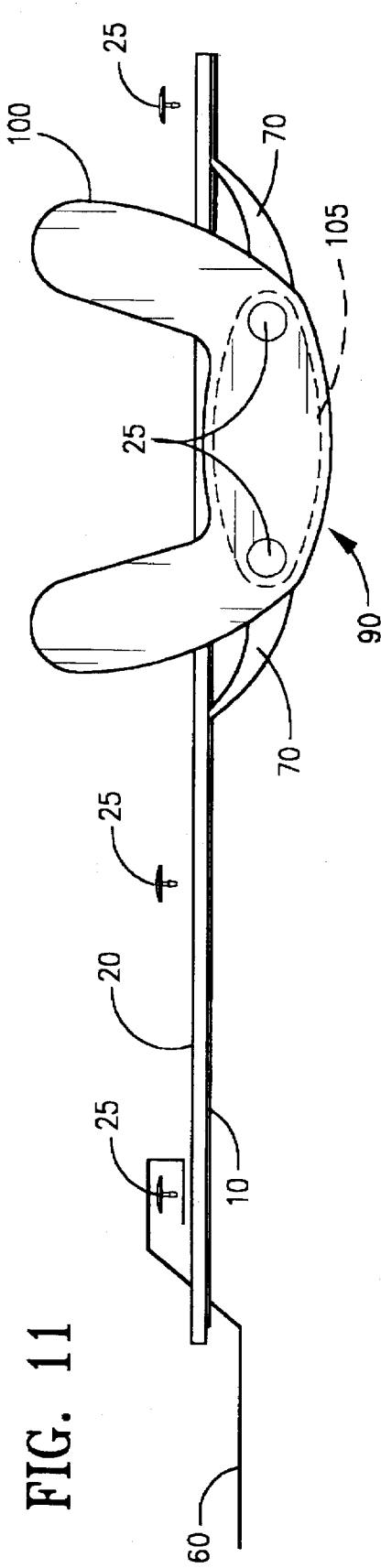
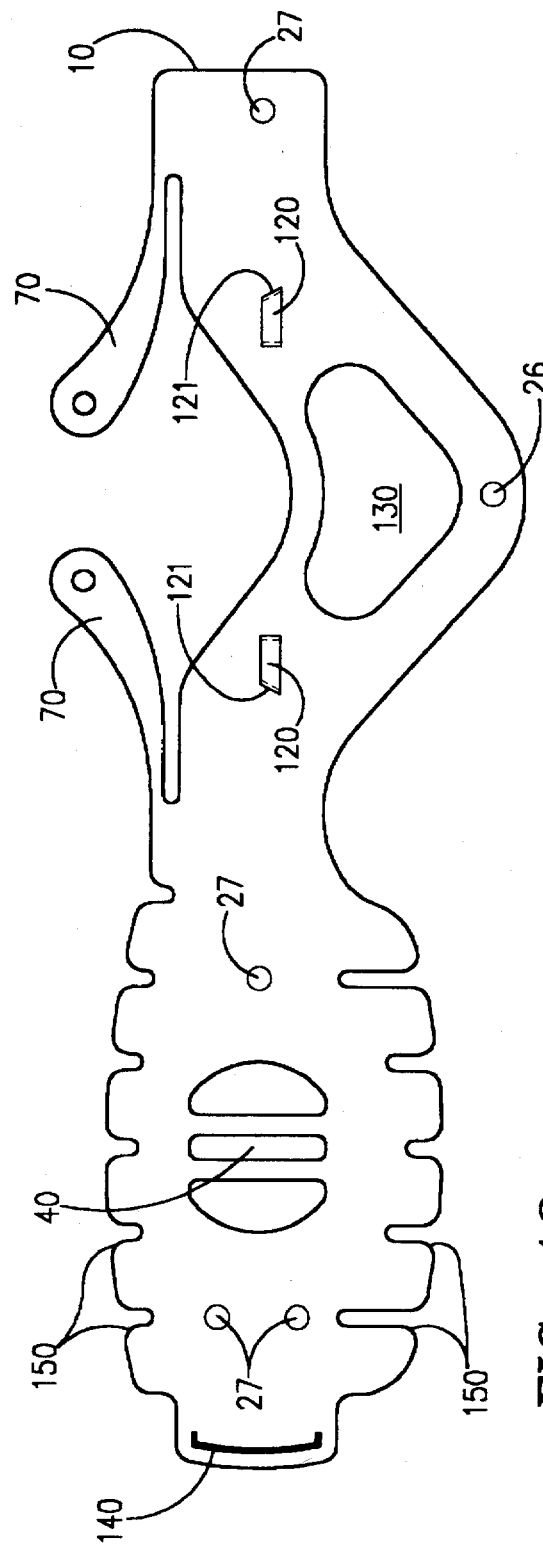
FIG. 11
FIG. 12

CERVICAL COLLAR

BACKGROUND OF THE INVENTION

1. Field of the Invention

This invention relates generally to the field of medical appliances and, specifically, to cervical collars.

2. Description of Related Art

Cervical collars are a popular and important medical appliance. Cervical collars are used by paramedics and doctors alike to stabilize the head and neck of patients to prevent damage to the spine and soft tissue in the neck immediately following traumatic injury, and then to prevent further damage and promote healing during the days and weeks following the injury. Cervical collars are typically either hard or soft. The hard collars are usually constructed of rigid plastic lined with closed-cell foam while the soft collars are made of an open celled foam covered with fabric.

In both types of cervical collars, but particularly with the hard collar, there has been the problem that the wide variation in patient neck sizes has necessitated the manufacture and stocking of a large number of different sizes of collars. This is inconvenient and costly in any setting, but particularly so in ambulance and paramedic services where space is at a premium and where the personnel involved have more pressing tasks than looking through a large number of collars for the right size collar.

For the foregoing reasons there has been a need for a hard cervical collar which has an improved ability to adjust for different size necks.

SUMMARY OF THE INVENTION

A cervical collar having improved adjustability is disclosed. The collar has a chin support which is movably attached to the collar such that the chin support can be moved up or down to accommodate either longer or shorter necks.

It is an object of the invention to provide a cervical collar which has an improved ability to be adjusted for different sizes of necks.

It is a further object of the invention to provide a cervical collar which will allow health care professionals to stock a lower number of total collars without diminishing the ability of those professionals to provide a properly fitting collar.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the claims.

BRIEF DESCRIPTION OF THE DRAWINGS

FIG. 4 is a top, plan view of the chin support.

FIG. 5 is an elevational view of one of the adjustable posts for the chin support.

FIG. 6 is a sectional view of one of the adjustable posts.

FIG. 7 is another sectional view of one of the adjustable posts.

FIG. 11 is a top, plan view of the invention.

FIG. 12 is an elevational view of a portion of the invention.

DESCRIPTION OF THE PREFERRED EMBODIMENT

Figure 1:
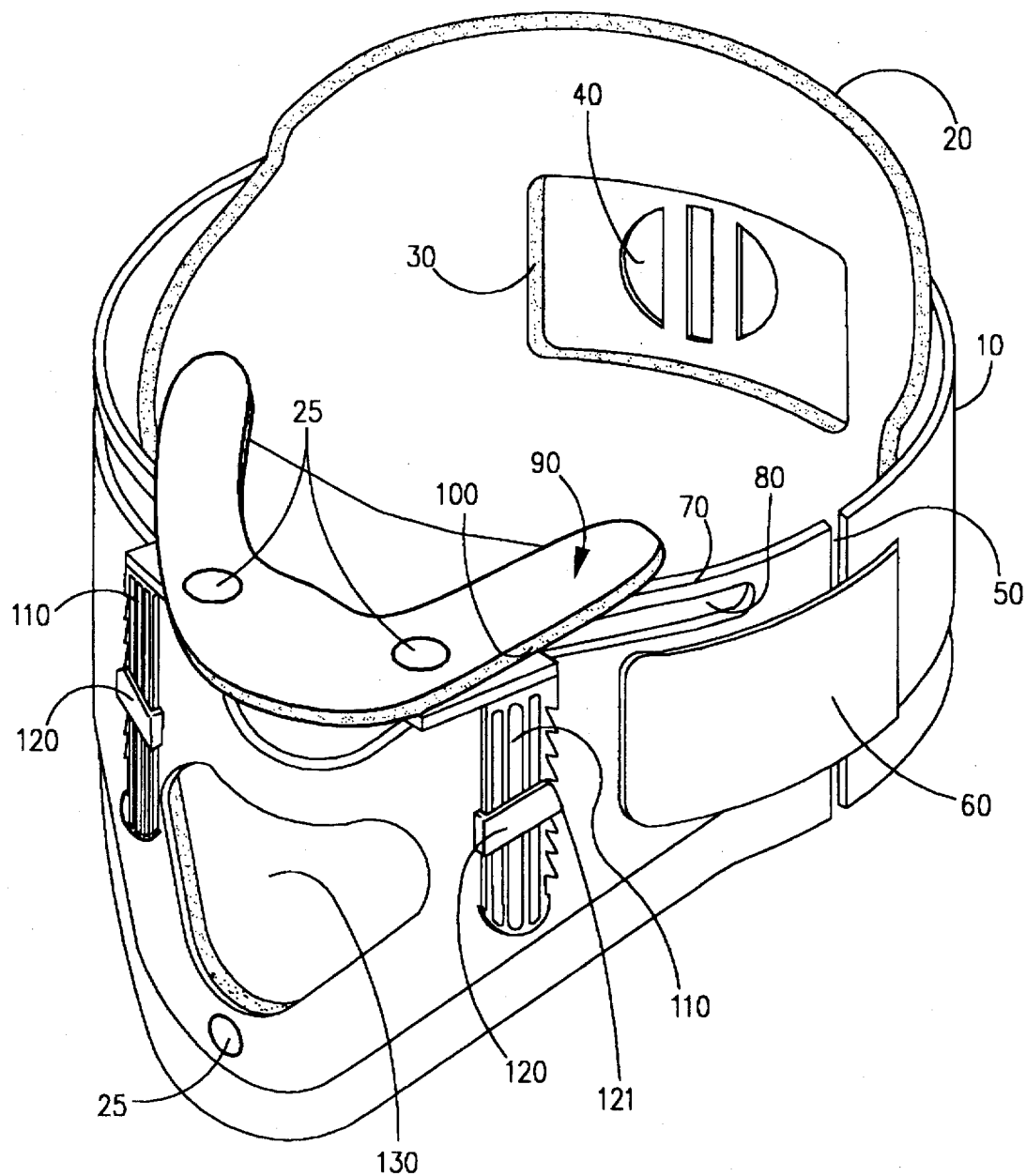
FIG. 1 is a perspective view of the invention.

FIG. 1 is a perspective view of the cervical collar as the collar would appear while being worn on a patient's neck. This figure shows a flexible plastic shell, 10, and a closed-cell foam lining, 20. The foam lining, 20, has a ventilation hole, 30, at the back of the lining, 20, which is placed over the ventilation hole, 40, in the back of the shell, 10. The shell, 10, and lining, 20, are shown attached by rivets, 25. The rivets, 25, may be either plastic or metal. In the alternative, the shell, 10, and lining, 20, could be connected by alternative means, such as adhesive or hook and loop fasteners. The shell, 10, and lining, 20, have a gap, 50, which allows the collar to be opened for placement on a patient's neck. The collar is held closed by a hook and loop fastener, 60, which allows the gap, 50, to be adjusted for varying circumferences of necks. The top, front of the shell, 10, has two flexible members, 70, separated from the rest of the shell, 10, by a gap, 80. There is also a chin support sub-structure, denominated generally as 90, showing a closed-cell foam padding, 100, connected to a base (not shown in this figure), as well as to adjustable posts, 110, by rivets, 25. The posts, 110, are slidably inserted into protruding channels, 120, on the shell, 10. The channels have an outer edge, 121, which is set at an angle to the opposite, inner edge of the channel, 120. There is also a delta-shaped opening, 130, in the front of the shell, 10, and lining, 20, which allows access to a patient's throat so that the patient's pulse can be checked or, if necessary, a tracheotomy or other procedure can be performed while the collar is in place on the patient's neck.

Figure 2:
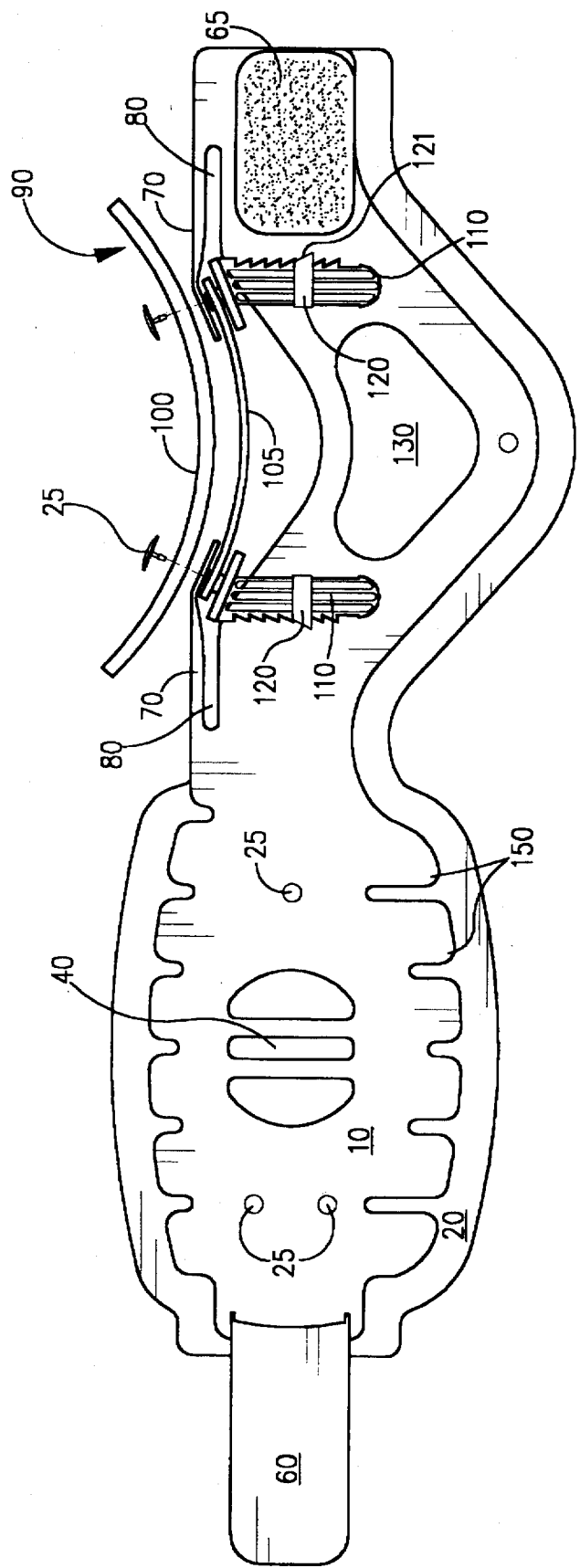
FIG. 2 is an elevational view of the invention in a fully open position.

Turning to FIG. 2, we see an elevational view of the collar in a fully open position. Once again, we see the shell, 10, and the lining, 20, held together with rivets, 25. We also see the ventilation hole, 40, the delta shaped opening, 130, the flexible members, 70, separated by gaps, 80, the adjustable posts, 110, the channels, 120, the foam padding, 100, and the strap, 60, as shown in FIG. 1. In FIG. 2, however, we can see that the chin support, 90, has a base, 105, which supports the foam padding, 100, on the chin support, 90. This figure shows that the base, 105, is placed on the top of the posts, 110. Next, the flexible members, 70, are placed over the base, 105, and the foam padding, 100, is placed on top of the entire chin support, 90, and held in place with rivets, 25. Accordingly, the chin support sub-structure, 90, can be moved up or down by sliding the adjustable posts, 110, up or down in the channels, 120. As the posts, 110, are moved up or down, the flexible members, 70, the base, 105, and the foam padding, 100, all move up or down as well. It is the up or down adjustment of the chin support, 90, which allows the collar to be fitted to patients with different neck lengths. This figure also shows a patch of hook and loop fabric, 65, which is permanently attached to the shell, 10, preferably by means of adhesive. FIG. 2 further shows an optional feature of the collar, specifically, the use of a plurality of tabs, 150, along the back of the shell, 10. The tabs, 150, add flexibility to the back of the shell, 10, but they also increase manufacturing costs and can be omitted if desired.

Figure 3:
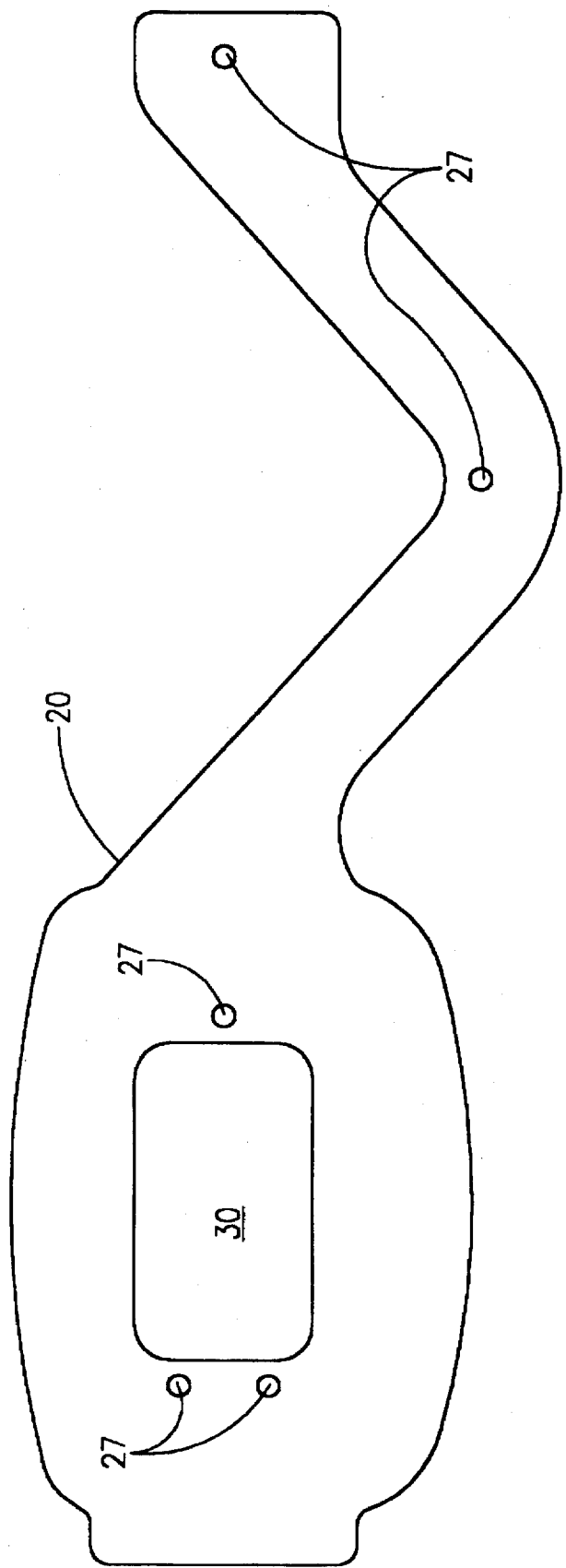
FIG. 3 is an elevational view of the interior foam liner.

FIG. 3 shows the foam lining, 20, removed from the shell, 10, and laid out in a fully open position. The lining, 20, has a number of holes, 27, for accommodating rivets, 25. The ventilation hole, 30, at the back of the lining, 20, is also visible in this figure.

FIG. 4 is a plan view of the foam padding, 100, showing rivet holes, 27. All of the foam parts of the collar are closed-cell foam in order to avoid the absorption of body fluids.

FIG. 5 is a front elevation of one of the adjustable posts, 110, showing a top portion, 160, and a bottom portion, 170, hingeably connected by a v-shaped groove, 180. The bottom portion, 170, is constructed of two I-shaped members, 190, separated by a slot, 200. The inner edge (where the inner edges of the posts, 110, are the edges which are nearest to the other post 110) of the bottom portion, 170, is smooth, while the outer edge, 220, of each post, 110, has a saw-tooth pattern. The saw-tooth patterned outer edge, 220, detachably engages the channel, 120. The slot, 200, allows the end-user of the collar to apply finger pressure to the inner and outer edges, 210 and 220, squeezing the I-shaped members, 190 towards each other and allowing the saw-toothed outer edge, 220, to disengage from the angled, outer edge, 121, of the channel, 120. An important feature is that the saw-tooth edge, 220, has individual teeth set at an angle equal to the angle of the outer edge, 121, of the channel, 120. FIG. 5 also shows a protrusion, 230, which aids in attaching the flexible members, 70, the base, 105, and the foam padding, 100, to the posts, 110, by means of rivets, 25.

FIG. 6 is a section of a post, 110, taken along the section indicated in FIG. 5. FIG. 6, gives a clearer picture of the v-shaped groove, 180. The groove, 180, is shaped such that the top portion, 160, can be hingeably folded forward toward the bottom portion, 170. This figure also gives a clearer view of the protrusion, 230. When the top portion, 160, is folded forward, the protrusion, 230 is pointed toward the top of the collar so that the protrusion, 230, is able to pass through the rivet holes, 27, in the base, 105, the flexible members, 70, and the foam padding, 100, and receive a rivet, 25.

FIG. 7 is another section of a post, 110, along the section as indicated in FIG. 5. In FIG. 7, one can see the cross-section of the I-shaped members, 190, separated by a slot, 200, as well as the inner edge, 210, and outer edge, 220.

Figure 8:
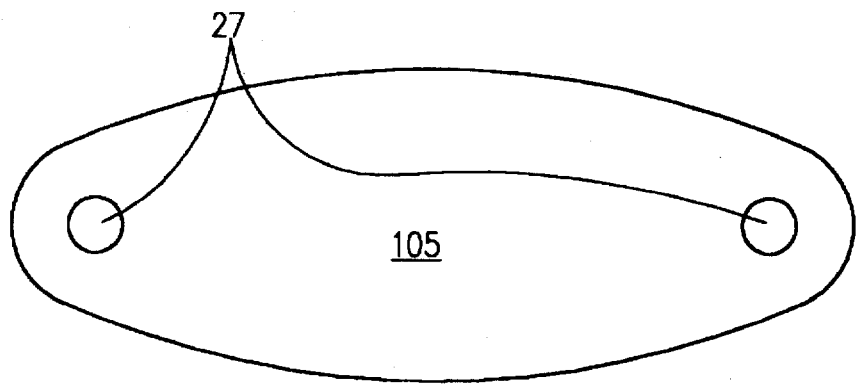
FIG. 8 is a top, plan view of a portion of the chin support.

FIG. 8 is a plan view of the base, 105, of the chin support, 110, showing the rivet holes, 27.

Figure 9:
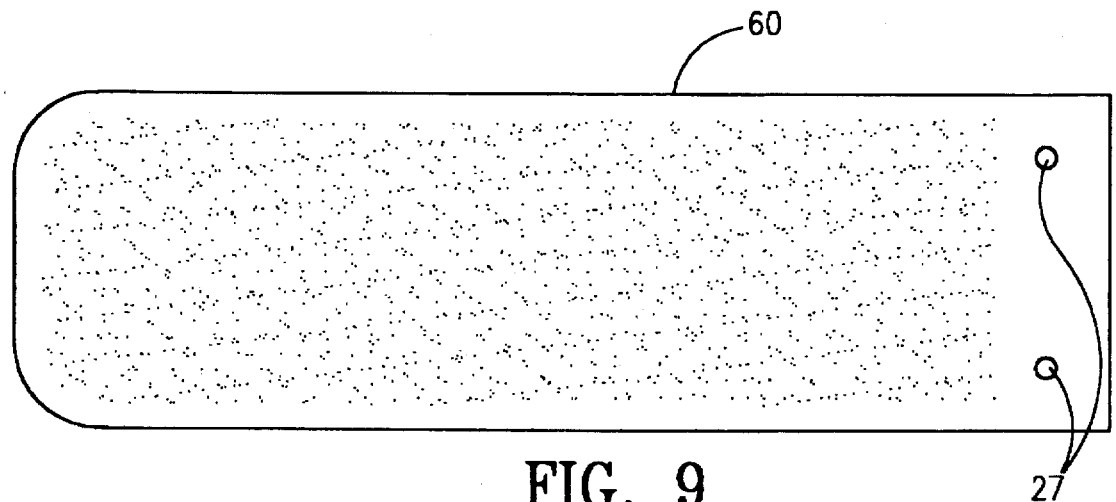
FIG. 9 is an elevational view of the hook and loop strap.

FIG. 9, is an elevation of the strap, 60, showing rivet holes, 27.

Figure 10:
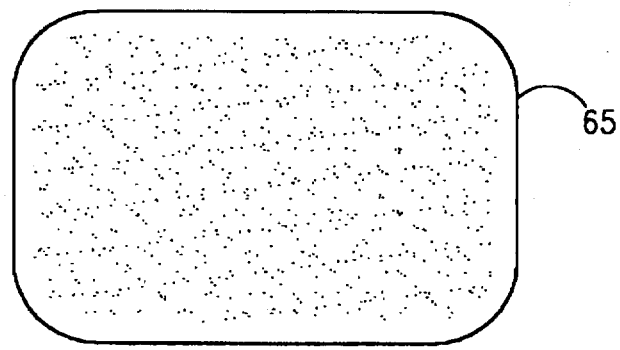
FIG. 10 is an elevational view of the hook and loop material which engages the strap.

FIG. 10 is an elevation of the patch of hook and loop fabric, 65.

FIG. 11 is a top, plan view of the collar showing the shell, 10, and the chin support sub-structure, 90. In this figure, we can see that the strap, 60, is attached to the shell, 10, and lining 20, by a rivet, 25. The strap, 60, is then folded back over the rivet, 25, before passing through a slit (not visible in this figure) in the collar. This figure also shows how the flexible members, 70, are twisted forward so as to engage the rivets, 25, in the chin support, 90.

FIG. 12 is a front elevation of the shell, 10. The shell, 10, has a plurality of rivet holes, 27, flexible members, 70, channels, 120, a delta-shaped opening, 130, in the front, and a ventilation opening, 40, in the back. The optional tabs, 150, are also shown. The slit, 140, for the strap, 60, is also visible on this figure. This figure also gives us the best view of the channels, 120, showing the angled outer edges, 121, which detachably engage the sawtooth-shaped outer edges, 220, of the posts, 110.

Each of the elements described above, or two or more together, may also find a useful application in other types of methods differing from the type described above. While certain novel features of this invention have been shown and described and are pointed out in the annexed claims, it is not intended to be limited to the details above, because various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A cervical collar comprising:
  a. a flexible plastic shell which can be formed into approximately a circular shape, wherein the shell has an inner surface and an outer surface as well as front and back portions;
  b. a ventilation opening at the back portion of the shell;
  c. an opening at the front portion of the shell suitable for providing access to a neck of a person wearing the collar;
  d. a closed-cell foam lining which fits along the inner surface of the shell, with openings in the lining corresponding to the openings in the shell;
  e. flexible members disposed at a top edge of the front portion of the shell;
  f. channels on the outer surface of the front portion of the shell;
  g. two adjustable posts, wherein each post has an inner edge and an outer edge, where each post is inserted into a channel and where the inner edge of each post is smooth and the outer edge of each post has a saw-tooth pattern which is suitable for detachably engaging the channel;
  h. a slot in each adjustable post to allow the user of the collar to squeeze the inner and outer edge of each post together by use of finger pressure thus allowing the outer edge of each post to disengage from the channel;
  i. a chin support attached to the posts and to the flexible members.

2. A cervical collar comprising:
  a. a flexible plastic shell which can be formed into approximately a circular shape, wherein the shell has an inner surface and an outer surface as well as front and back portions;
  b. a ventilation opening at the back portion of the shell;
  c. an opening at the front portion of the shell suitable for providing access to a neck of a person wearing the collar;
  d. a closed-cell foam lining which fits along the inner surface of the shell, with openings in the lining corresponding to the openings in the shell;
  e. flexible members disposed at a top edge of the front portion of the shell;
  f. channels on the outer surface of the front portion of the shell;
  g. two adjustable posts, wherein each post has an inner edge and an outer edge as well as a top portion and a bottom portion, where each post is inserted into a channel and where the inner edge of each post is smooth and the outer edge of each post has a saw-tooth pattern which is suitable for detachably engaging the channels;

h. a groove between the top portion and the bottom portion of each post which allows the top portion of each post to be folded toward the bottom portion of each post;

i. a slot in each adjustable post to allow the user of the collar to squeeze the inner and outer edge of each post together by use of finger pressure thus allowing the outer edge of each post to disengage from the channel;

j. a chin support attached to the posts and to the flexible members.

3. A cervical collar comprising:

a. a flexible plastic shell which can be formed into approximately a circular shape, wherein the shell has an inner surface and an outer surface as well as front and back portions;

b. a ventilation opening at the back portion of the shell;

c. an opening at the front portion of the shell suitable for providing access to a neck of a person wearing the collar;

d. a closed-cell foam lining which fits along the inner surface of the shell, with openings in the lining corresponding to the openings in the shell;

e. flexible members disposed at a top edge of the front portion of the shell;

f. two channels on the outer surface of the front portion of the shell where each channel has an angled outer edge;

g. two adjustable posts, wherein each post has an inner edge and an outer edge as well as a top portion and a bottom portion, where each post is inserted into a channel and where the inner edge of each post is smooth and the outer edge of each post has a saw-tooth pattern which is suitable for detachably engaging the angled outer edge of each channel;

h. a groove between the top portion and the bottom portion of each post which allows the top portion of each post to be folded toward the bottom portion of each post;

i. a slot in each adjustable post to allow the user of the collar to squeeze the inner and outer edge of each post together by use of finger pressure thus allowing the outer edge of each post to disengage from the channel;

j. a chin support base, having top and bottom portions, attached to the posts and to the flexible members;

k. closed cell foam padding attached to the top portion of the chin support base.

* * * * *